US005654166A

United States Patent [19]
Kurth

[11] Patent Number: 5,654,166
[45] Date of Patent: Aug. 5, 1997

[54] PROCESS OF PREPARING HORMONE-FREE BOVINE CARTILAGE FOR DOSAGE FORM

[76] Inventor: Gerhard P. Kurth, 1117 E. Putnam Ave., Riverside, Conn. 06878

[21] Appl. No.: 615,947

[22] Filed: Mar. 14, 1996

Related U.S. Application Data

[63] Continuation-in-part of Ser. No. 302,518, Nov. 9, 1994, Pat. No. 5,503,990.

[51] Int. Cl.$^6$ .................................................. C12P 21/00
[52] U.S. Cl. ............................................ 435/68.1; 424/528
[58] Field of Search ............................ 435/68.1; 424/528

[56] References Cited

U.S. PATENT DOCUMENTS 5,503,990  4/1996  Kurth ..................................... 435/68.1

Primary Examiner—Herbert J. Lilling

[57] ABSTRACT

The present invention relates to a significant improvement in the preparation of a pharmaceutically purified and proven effective product of powdered bovine tracheal cartilage for the treatment of a number of maladies, including such cancers as disclosed in U.S. Pat. No. 4,822,607 and as a food supplement product. This improvement in the process of preparation is a continuation-in-part of my U.S. patent application Ser. No. 08/302,518 filed Nov. 9, 1994, now U.S. Pat. No. 5,503,990. The present improvement over the above referenced U.S. patent application, which is considerably less expensive, is accomplished by replacing the final cryogenic milling process with a new step including subjecting the processed cartilage to an ACM pulverizer mill, then to a Tenberg B cyclone, while the fine dust is collected by a fine dust bag and the cartilage powder is collected and sent to packaging and/or encapsulation.

6 Claims, No Drawings

PROCESS OF PREPARING HORMONE-FREE BOVINE CARTILAGE FOR DOSAGE FORM

RELATED APPLICATION

This application is a continuation-in-part of U.S. patent application Ser. No. 08/302,518 filed Nov. 9, 1994, entitled "Improvement in the Preparation of A Health Food Supplement Product", now U.S. Pat. No. 5,503,990.

FIELD OF THE INVENTION

The present invention relates to an improvement over the preparation disclosed in the process described in the above referenced related application and as disclosed and patented by Balassa & Prudden in their U.S. Pat. No. 4,822,607, issued 18 Apr. 18, 1989 and by the same J. F. Prudden's publication in The Journal of Biological Response Modifiers, Vol. 6, 1985. The improvement of the present invention allows for a product that is more efficiently and more effectively produced.

REFERENCES TO RELATED ART

The following art has been found to be related to the field of the present invention but in no way do any of the herein cited references anticipate or even suggest the novel advance in the art that is made by the process of the present invention.

U.S. Pat. No. 4,822,607 and in an article by J. F. Prudden in the Journal of Biological Response Modifiers, Vol. 6, 1985, entitled "Treatment of Human Cancer with Agents from Bovine Cartilage, by J. F. Prudden, department of Surgery, Doctors Hospital, New York, N.Y. 21 Jun. 1985, the process described in both of the above references will be directly compared to the novel process of the present invention.

OBJECTS OF THE INVENTION

An object of the present invention is to provide a new and novel process to prepare a hormone-free pharmaceutical grade of hormone-free bovine cartilage product.

Another object of the present invention is to provide a new and novel process to prepare a pharmaceutical grade of bovine cartilage that is less expensive and less time consuming then the present process.

A further object of the present invention is to provide a new and novel process to prepare a pharmaceutical grade of bovine cartilage that will allow for the elimination of cryogenic milling that was necessary previously to obtain the quality of product to be of pharmaceutical grade.

Various other objects, advantages and features of the new and improved process of the present invention will become apparent to those skilled in the art from the previous and the following discussions contained herein.

SUMMARY OF THE INVENTION

The present invention is a significant improvement in the process of preparing extremely finely divided, pharmaceutical grade bovine cartilage in a very close uniform particle size as described and patented in my U.S. Pat. No. 5,503,990. The improvement of the present invention over the process described in my U.S. Patent, supra., involves the replacement of the final step in my patented process of cryogenic milling with the much less expensive final step. In this process step the chopped Bovine trachea cartilage that has been enzymatically digested and delipidized (defatted) is subjected to an ACM Pulverisor and then to a cyclone particle size reducer and uniform size producer. The dust that is produced in said cyclone is drawn off to a fine dust collection bag. This prevents the final product from being contaminated and the work place becoming a hygiene problem. After the prepared powder of the pulverizer is collected, it is then packaged in capsule or in packet form.

The ACM Pulverisor is made by Mikro AMC a subsidiary of Hosokuwu Micron Powder Systems of Summit, N.J. The cyclone is a model Tenberg B for fine powders. This cyclone is a matter of choice and may be replaced with any other dust collector and remover with suitable characteristics The cyclone is a model Tenberg B from Waitaki Biosciences International Ltd., Christchurch, New Zealand.

The present invention is a substantial improvement over the old process that is claimed and described in my U.S. Pat. No. 5,503,990 and is presently being used to prepare pharmaceutical grade bovine cartilage in dosage form as disclosed in J. F. Prudden's works, such as his article "The Treatment of Human cancer with Agents Prepared from Bovine Cartilage" referred to supra.

The previously available bovine cartilage preparation processes and the process described in my U.S. Pat. No. 5,503,990, which respectively are ball milling, which produces non uniform product size and secondly cycrogenic milling, which is very costly and time consuming, both are significally more expensive in commercial applications. The finely divided, uniform particle size of purified pharmaceutical grade bovine cartilage that is necessary to attain the effectiveness and commercial economy of the product prepared by the process of the present invention is accomplished by replacing the final step in the two prior processes with pulverisor milling and cyclone particle size reduction which delivers a product that is much more uniform in size and much more economical to produce.

The product produced by the new process of the present invention is novel because of its predictability in particle size and because the present process reduces the effort and cost in producing the required pharmaceutical grade final product.

DESCRIPTION OF THE PREFERRED EMBODIMENT OF THE PRESENT INVENTION

The raw tracheal cartilage may be prepared for processing using cartilage particle size of about 750 microns that have been reduced to from about 10 to about 150 microns by any of the suitable methods as taught by the art. Such methods of the art are disclosed in U.S. Pat. Nos. 3,400,199 (U.S. Pat. No. Re. 28,093), 3,966,908 and 4,822,607.

The new and improved process of the present invention is accomplished by producing considerably more reliable and predictable uniform particle size and accomplishing same more economically and in a shorter period of time. This is accomplished by replacing the final step of the prior art, namely ball milling and replacing the final step in the process disclosed in my U.S. Pat. No. 5,503,990, namely impact milling coupled with cryogenic particle size reduction. The new and novel final step of the present invention is a combination of subjecting the cartilage from which the lipid (fat) has been removed first to a ACM Pulverisor, model 10 from Hosokuwu and then placed in a cyclone for fine powders, model B-Tenberg, available from Waitaki Biosciences International, Christchurch, NZ. The two treatments of the final step of the present invention will be discussed in greater detail later in this specification.

In the prior art and in the present invention the average size of each finely divided hormone-free bovine tracheal cartilage particle that is used in step 1 is not critical and successful extracts have been prepared using particle sizes up to about 12 mm sq. However, it has been found that more effective extractions can be obtained with the use of bovine tracheal cartilage in sizes of from about 1 mm sq. to about 3 mm sq.

DETAILED DESCRIPTION OF THE PROCESS OF THE PRESENT INVENTION

In order to more clearly point out the improvement of the new and novel process of the present invention comparison is made with the prior art and the process disclosed in my U.S. Pat. No. 5,503,990, with the process of the present invention, which accomplishes all of the stated objects of this invention as pointed out supra,

TABLE 1

| Process of the Art | Process of U.S. | Present Invention |
| --- | --- | --- |
| Step 1. Chopped Bovine Trachea in size 8–12 mm | Chopped Bovine Trachea in size of about 1 to 3 mm | Chopped B. Trachea in size of about 1–3 mm |
| Step 2. Enzymatic Digestion | Enzymatic Digestion | Enzymatic Digestion |
| Step 3. Lipid (fat) Removal | Lipid (fat) Removal | Lipid (fat) Removal |
| Step 4. Ball Milling at ambient temp. | Cryogenic Milling at about 50 C | ACM Pulverizing to fine powder & dust col. |

As can be seen from Table 1 supra., Steps 1 differ somewhat, Steps 2 and Steps 3 differ very little if at all. However, it is in Step 4 that a complete difference exist between all three processes and it is in this step in which the novelty of the present invention lies. An explanation of the processes of Steps 1, 2, 3 and 4 follows hereinafter:

Step 1. Raw bovine tracheal cartilage is washed and frozen at −70 degrees C. to prevent bacterial load. The washed and frozen trachea is stored until use. It is then thawed and mechanically trimmed of all adhering tissue, then cut into small chunks to a size of between 8 mm and 12 mm for the process of the prior art and to a size of from about 1 mm to about 3 mm in the process of my U.S. Pat. No. 5,503,990 and the process of the improvement of the present invention, which is less expensive and less time consuming.

Step 2. The Enzymatic digestion is accomplished by subjecting the chopped tracheal cartilage to the enzymatic action of Pepsin for the purpose of digesting unwanted protein. Since Pepsin is quite acid in its pH, the pH in this step must be continuously monitored and adjusted in order to maintain a constant pH of between about 6.5 and 8.0. When the enzymatic action is complete, the treated chopped tracheal cartilage is carried on to step 3.

Step 3. The lipid fat is removed from the enzyme treated tracheal cartilage by the use of the solvent Acetone ($CH_3COCH_3$). As can be seen, up to this point the process of the prior art, the process of my U.S. Pat. No. 5,503,990 and the process of the present invention are relatively similar except for the size of the tracheal cartilage in Step 1 where it has been found that a more consistent final product is produced when the starting tracheal cartilage is in the range of from about 1 mm to about 3 mm in size. As in my U.S. Pat. No. 5,503,990, the present invention is in the final step, step 4, and it is a significant improvement over the final step 4 of the process of my U.S. Pat. No. 5,503,990 as well as the older prior art process.

Step 4. This is the step that produces the final product that is to be packaged and delivered to the public for ingestion. In the prior art, the cleaned chopped tracheal cartilage is subjected to ball milling which is well known to those skilled in the art. Ball milling produces the desired reduction in size but the uniformity of particle size is not at all reliable nor desirable and requires additional classification to remove the remaining large particles. It is also time consuming and expensive to produce the final product by the process of the prior art. The process of cryogenic milling is disclosed in my U.S. Pat. No. 5,503, 990.

While the present process produces a product that is far superior and less expensive than the process of the prior art, the present invention produces the same quality product much less expensively and cost effectively. Step 4 of the present invention consists of an ACM pulverizing step and a cyclone fine particle redusing step. The following are the details of the Step 4 improvement in the processes: this final step is two phases although they both accrue at almost the same time. The first phase is taking the chopped and cleaned cartilage, which are now flakes of about 3ram in size and subjecting said flakes to an ACM oulverisor by Hosokuwu Industries, at about 30 degrees C. The pulverizer is equipped with an internal classifier for size selection. This requires an air supply for operation of the pulverizer. Large particles are rejected by the internal classifier and internally recycled past the pulverizing hammers until ground down to the required size. As the particles reach the required size they are passed to the Tenberg B cyclone where powder is collected into bags for sending to encapsulation. In addition, a very fine dust bag is associated with the cyclone and collects very fine dust powder (<1.0% by weight) that is carried off from the cyclone. This dust bag prevents the fine dust from being a hygiene problem in the pulverizing/cycloning facility. The dust bag is made of polyester or like material. The final bovine cartilage product is off-white and in a size of about 90% below 150 microns. The internal air flow maintains a low product temperature and results in more uniform particle size. The lower cost of this final step of the process results in a more cost effective product.

While the description supra., contains many specificities, the reader should not construe these to be limitations on the scope of the invention, but merely as exemplifications of a preferred embodiment of the present invention. Those skilled in the art will envision that many other possible variations are within the scope of the present invention. For example, skilled artisans will readily be able to change the dimensions and the materials of the various embodiments. They can make many variations on the design of the present invention. Accordingly, the reader is requested to determine the scope of the present invention only by the scope of the appended claims and their legal equivalents, taken in view of the scope of this specification, and not by the examples that have been given herein.

What is claimed is:

1. A process of preparing a finely divided bovine trachea cartilage for dosage form of uniform size comprising the following steps:

a. providing said cartilage in chopped form, b. subjecting chopped cartilage to an enzymatic reduction process to remove protein and fat, c. removing the remaining fat from said reduced cartilage, d. reducing the cleaned cartilage to dosage form size by air operation pulverizing to maintain an operation temperature below 20 degrees C., cycloning the pulverized cartilage, removing contaminating dust and collecting powdered cartilage for encapsulation and packaging.

2. The process of claim 1 wherein said cartilage is chopped to a size of from about 1 mm to about 3 mm sq., prior to enzymatic action.

3. The process of claim 2 wherein protein is removed from said trachea cartilage by the action of pepsin.

4. The process of claim 3 wherein fat is removed from said trachea cartilage by the action of acetone.

5. The process of claim 4 wherein said air operating pulverizing temperature is in the range of from about 14 degrees C. and about 18 degrees C.

6. The process of claim 1 wherein said cartilage is chopped, prior to enzymatic reduction, to a size of from about 1 mm to about 3 mm, said protein is removed from said cartilage by the action of pepsin, said fat is removed by the action of acetone and said air operated pulverizing is carried out in a temperature range of from 14 degrees C. to about 18 degrees C., after cycloning and dust removal, said powdered tracheal cartilage is removed for encapsulation and packaging.

* * * * *